United States Patent [19]

Kisida et al.

[11] Patent Number: 4,980,373

[45] Date of Patent: Dec. 25, 1990

[54] HYDRAZONE COMPOUND AND PRODUCTION THEREFOR, AND AN INSECTICIDAL COMPOSITION CONTAINING THE SAME

[75] Inventors: Hirosi Kisida; Kenichi Mikitani, both of Takarazuka; Yoko Torisu, Ashiya; Tomotoshi Imahase, Takarazuka; Sumio Nishida, Tokyo, all of Japan

[73] Assignee: Sumitomo Chemical Company, Limited, Osaka, Japan

[21] Appl. No.: 395,516

[22] Filed: Aug. 18, 1989

[30] Foreign Application Priority Data

Aug. 26, 1988 [JP] Japan .................................. 63-212703

[51] Int. Cl.$^5$ ...................... A01N 44/04; C07C 143/68
[52] U.S. Cl. ........................................ 514/517; 558/54
[58] Field of Search ............................ 558/54; 514/517

[56] References Cited

U.S. PATENT DOCUMENTS 3,375,271 3/1968 Catino et al. .
3,732,307 5/1973 Middleton .
4,331,680 5/1982 Giles et al. .
4,344,893 8/1982 Copping et al. .
4,394,387 7/1983 Copping et al. .
4,432,994 2/1984 Giles et al. .

FOREIGN PATENT DOCUMENTS 0003913 9/1979 European Pat. Off. .
0026040 4/1981 European Pat. Off. .

*Primary Examiner*—Nicky Chan
*Attorney, Agent, or Firm*—Birch, Stewart, Kolasch & Birch

[57] ABSTRACT

A compound of the formula:

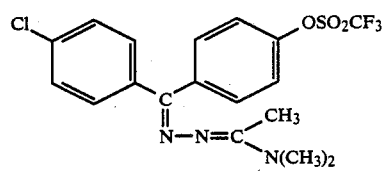

which is useful as an insecticide.

3 Claims, No Drawings

HYDRAZONE COMPOUND AND PRODUCTION THEREFOR, AND AN INSECTICIDAL COMPOSITION CONTAINING THE SAME

The present invention relates to a hydrazone compound and production therefor, and an insecticidal composition containing the same.

Numerous compounds have heretofore been used as insecticides. However, their use in large doses is generally required for production of a satisfactory insecticidal effect, and their insecticidal spectrum is not sufficiently broad. In addition, their insecticidal effect is, even if once remarkable, lowered with development of insects tolerable thereto.

As disclosed in EP-A1-003913 and EP-A1-026040, some hydrazone compounds are known to exert an insecticidal activity. However, their efficacy is not necessarily satisfactory with respect to insecticidal activity as well as insecticidal spectrum As a result of the extensive study seeking an insecticide having an excellent efficacy, it has now been found that a hydrazone compound of the formula

(I)

exhibits a prominent insecticidal activity with a fairly broad insecticidal spectrum. The present invention is based on this finding.

EP-A1-026040 as above-mentioned discloses a very broad scope of hydrazone compounds in which said hydrazone compound (I) falls. However, said hydrazone compound (I) itself is not specifically disclosed therein. Further, the insecticidal potency of said hydrazone compound (I) is much higher than that of the hydrazone compounds similar thereto in chemical structure as specifically disclosed in said literature.

Specific examples of the harmful insects against which the hydrazone compound (I) exerts its insecticidal activity are Lepidoptera (e.g. diamondback moth, rice stem borer, rice leafroller, cabbage armyworm, rice looper, common white, casemaking clothes moth, webbing clothes moth), Diptera (e.g. common mosquito, Anopheles mosquito, house fly), Orthoptera (e.g. German cockroach, smokybrown cockroach, brown cockroach, American cockroach), Formicidae (e.g. field ant, pavement ant, carpenter ant, fire ant), Coleoptera (e.g. southern corn root worm, northern corn root worm, chafers), Hymenoptera, Homoptera, Dictyoptera, etc. Their efficacy extends to harmful insects having developed resistance to conventional insecticides.

The hydrazone compound (I) of the invention can be produced by various procedures, of which typical examples are shown below:

Procedure (A):

The hydrazone compound (I) can be produced by reacting a compound of the formula:

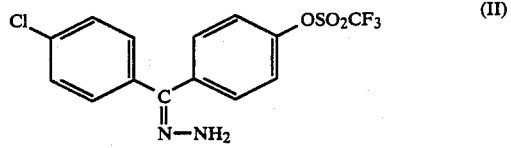
(II)

with a compound of the formula:

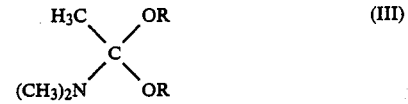
(III)

wherein R is a lower alkyl group.

The reaction is usually carried out by treating 1 mole of the compound (II) with 1 to 50 moles of the compound (III) at a temperature of room temperature to 200° C., preferably of 50 to 150° C., for a period of 5 minutes to 100 hours, preferably of 30 minutes to 50 hours. The solvent is not necessarily required to use. When used, it may be chosen from ethers (e.g. diethyl ether, tetrahydrofuran, dioxane), alcohols (e.g. ethylene glycol, glycerin, methanol, ethanol), acid amides (e.g. N,N-dimethylformamide, N,N-dimethylacetamide), aromatic hydrocarbons (e.g. benzene, toluene, chlorobenzene), halogenated hydrocarbons (e.g. methylene chloride, chloroform), nitriles (e.g. acetonitrile), water, etc. Their mixture is also usable. If necessary, a catalyst may be used in an amount of 0.001 to 1 mole to 1 mole of the compound (II), and examples of the catalyst are mineral acids (e.g. hydrochloric acid, sulfuric acid, nitric acid), organic acids (e.g. formic acid, acetic acid, propionic acid, methanesulfonic acid, benzenesulfonic acid, p-toluenesulfonic acid), acid addition salts of amines (e.g. pyridine hydrochloride, triethylamine hydrochloride), etc.

After completion of the reaction, the reaction mixture is subjected to post treatment in a per se conventional manner to recover the objective product.

Procedure (B):

The hydrazone compound (I) is obtainable by reacting a compound of the formula:

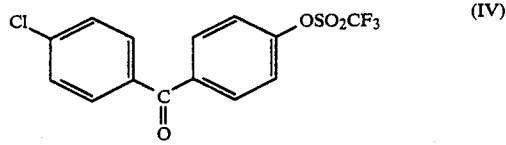
(IV)

with a compound of the formula:

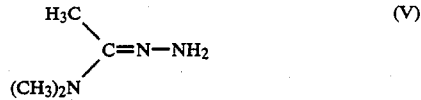
(V)

Usually, the reaction is effected by treating 1 mole of the compound (IV) with 0.5 to 10 moles of the compound (V) at a temperature of −20 to 200° C., preferably of −10 to 150° C., for a period of 5 minutes to 300 hours, preferably of 5 minutes to 120 hours. When the use of a solvent is desirable, it may be chosen from ethers (e.g. diethyl ether, tetrahydrofuran, dioxane), alcohols (e.g. ethylene glycol, glycerin, methanol, ethanol), acid amides (e.g. N,N-dimethylformamide, N,N-dimethylacetamide), sulforan, dimethylsulfoxide, aromatic hydrocarbons (e.g. benzene, toluene, chlorobenzene), halogenated hydrocarbons (e.g. methylene chloride, chloroform), aliphatic hydrocarbons (e.g. n-pentane, n-hexane, n-heptane), alicyclic hydrocarbons (e.g. cyclohexane), pyridines (e.g. pyridine, picoline), acetic acid, water, etc. Their mixture is also usable. If necessary, a catalyst may be present in the reaction system in an amount of 0.001 to 1 mole to 1 mole of the compound (IV), and its examples are mineral acids (e.g. hydrochloric acid, sulfuric acid, nitric acid), organic acids (e.g. formic acid, acetic acid, propionic acid, methanesulfonic acid, benzenesulfonic acid, p-toluenesulfonic acid), acid addition salts of amines (e.g. pyridine hydrochloride, triethylamine hydrochloride), etc.

After completion of the reaction, the reaction mixture is subjected to post-treatment in a per se conventional manner to recover the objective product.

Procedure (C):

The hydrazone compound (I) is obtained by reacting a compound of the formula:

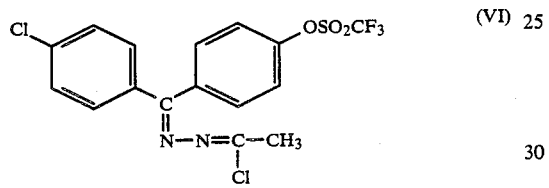

with dimethylamine.

The reaction is normally performed by treating 1 mole of the compound (VI) with 1 to 100 moles of dimethylamine at a temperature of −20 to 200° C., preferably of 0 to 100° C., for a period of 5 minutes to 100 hours. When desired, a solvent chosen from aromatic hydrocarbons (e.g. benzene, toluene, xylene, chlorobenzene, 0-dichlorobenzene, pyridine), halogenated hydrocarbons (e.g. chloroform, carbon tetrachloride, 1,2-dichloroethane, 1,1,1-trichloroethane, tetrachloroethylene, trichloroethylene), aliphatic hydrocarbons (e.g. n-hexane, n-heptane), alicyclic hydrocarbons (e.g. cyclohexane), water, etc. may be used. Their mixture is also usable.

After completion of the reaction, the reaction mixture is subjected to ordinary post-treatment to give the objective product.

Procedure (D):

The hydrazone compound (I) is produced by reacting a compound of the formula:

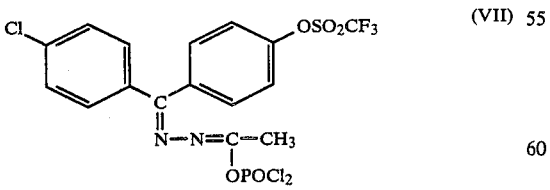

with dimethylamine.

The reaction may be performed substantially in the same manner as in Procedure (C). Namely, it can be accomplished by treating 1 mole of the compound (VII) with 1 to 100 moles of dimethylamine at a temperature of −20 to 200° C., preferably of 0 to 100° C., for a period of 5 minutes to 100 hours. If desired, any solvent chosen from aromatic hydrocarbons (e.g. benzene, toluene, xylene, chlorobenzene, 0-dichlorobenzene, pyridine), halogenated hydrocarbons (e.g. chloroform, carbon tetrachloride, 1,2-dichloroethane, 1,1,1-trichloroethane, tetrachloroethylene, trichloroethylene), aliphatic hydrocarbons (e.g. n-hexane, n-heptane), alicyclic hydrocarbons (e.g. cyclohexane), water, etc. may be employed. Their mixture can also be employed.

After completion of the reaction, the reaction mixture is subjected to ordinary post-treatment to recover the objective product.

In the above Procedures, the starting compounds (II) and (IV) are known and can be produced, for instance, in the manner as disclosed in EP-A1-026040. Also, the compounds (III) and (V) are commercially available in the market and may be produced according to the known method.

The compounds (VI) and (VII) are novel. The compound (VI) may be produced, for instance, by reacting a compound of the formula:

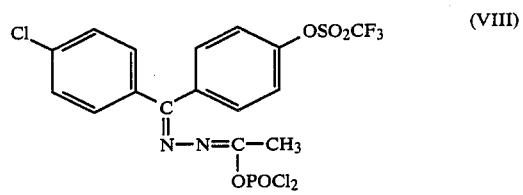

with phosphorus pentachloride. Likewise, the compound (VII) may be produced by reacting the compound (VIII) with phosphorus oxychloride.

In these reactions, the reagent such as phosphorus pentachloride or phosphorus oxychloride is normally used in an amount of 1 to 5 moles to one mole of the compound (VIII). In case of using phosphorus pentachloride as the reagent, the reaction may be performed at a temperature of room temperature to 250° C., preferably of 100 to 180° C., for a period of 5 minutes to 100 hours. In case of using phosphorus oxychloride as the reagent, the reaction may be effected at a temperature of 0 to 250° C., preferably of 10 to 180° C., for a period of 5 minutes to 100 hours. When desired, any inert solvent may be used in each of those reactions, and examples of the solvent are aromatic hydrocarbons (e.g. benzene, toluene, xylene, chlorobenzene, 0-dichlorobenzene), halogenated hydrocarbons (e.g. chloroform, carbon tetrachloride, 1,2-dichloroethane, 1,1,1-trichloroethane, tetrachloroethylene, trichloroethylene), aliphatic hydrocarbons (e.g. n-hexane, n-heptane), alicyclic hydrocarbons (e.g. cyclohexane), etc. Their mixtures are also usable.

The reaction mixture is subjected to post-treatment in a conventional manner to recover the compound (VI) or (VII) as produced, which may be used as the starting material in Procedure (C) or (D) with or without further purification.

The compound (VIII) is known and can be produced, for instance, by the procedure as disclosed in EP-A1-026040.

The hydrazone compound (I) has two geometrical isomers attributed to the steric configuration of the double bond in the hydrazone structure. Each of those geometrical isomers as well as their mixture are within the scope of this invention, and any of them may be used as an insecticide.

On the application of the hydrazone compound (I) as an insecticide, it may be used as such. Normally, however, it is incorporated, if necessary, together with any auxiliary agent, into a solid, liquid or gaseous carrier or diluent or a bait to make an appropriate preparation form such as an oil spray, an emulsifiable concentrate, a wettable powder, a flowable, granules, a dust, an aerosol, a fumigant, toxic baits or the like. In those preparations, the hydrazone compound (I) is usually contained in a concentration of about 0.01 to 95% by weight.

Examples of the solid carrier or diluent are clays (e.g. kaolin clay, diatomaceous earth, synthetic hydrated silica, bentonite, fubasami clay, terra alba), talcs, ceramics, other inorganic minerals (e.g. sericite, quartz, sulfur, active carbon, calcium carbonate, hydrated silica), chemical fertilizers (e.g. ammonium sulfate, ammonium phosphate, ammonium nitrate, urea, ammonium chloride), etc. Examples of the liquid carrier or diluent are water, alcohols (e.g. methanol, ethanol), ketones (e.g. acetone, methylethylketone), aromatic hydrocarbons (e.g. benzene, toluene, xylene, ethylbenzene, methylnaphthalene), aliphatic hydrocarbons (e.g. hexane, kerosene, lamp oil), alicyclic hydrocarbons (e.g. cyclohexane), esters (e.g. ethyl acetate, butyl acetate), nitriles (e.g. acetonitrile, isobutyronitrile), ethers (e.g. diisopropyl ether, dioxane), acid amides (e.g. N,N-dimethylformamide, N,N-dimethylacetamide), halogenated hydrocarbons (e.g. dichloromethane, trichloroethane, carbon tetrachloride), dimethylsulfoxide, botanical oils (e.g. soybean oil, cotton-seed oil), etc. Examples of the gaseous carrier, i.e. a propellant, are Freon gas, butane gas, LPG (liquefied petroleum gas), dimethyl ether, carbon dioxide, etc.

As the auxiliary agent, there are exemplified surfactants, adherents or dispersants, stabilizers, etc. The surfactants usable for emulsification, dispersion or spreading may be any of ionic and non-ionic types. Their examples are alkylsulfates, alkylsulfonates, arylsulfonates, dialkylsulfosuccinates, polyoxyethylene alkylaryl ether phosphates, naphthalenesulfonic acid formalin condensates, polyoxyethylene alkyl ether, polyoxyethylene polyoxypropylene block copolymers, sorbitan fatty acid esters, polyoxyethylene sorbitan fatty acid, etc. Examples of the adherents or dispersants may include casein, gelatin, polysaccharides (e.g. starch, arabic gum, cellulose derivatives, alginic acid), lignin derivatives, bentonite, saccharides, synthetic water-soluble polymers (e.g. polyvinyl alcohol, polyvinylpyrrolidone, polyacrylic acid), etc. As the stabilizers, there may be used alkyl phosphates (e.g. PAP (isopropyl acid phosphate), BHT (2,6-di-t-butyl-4-methylphenol), BHA (mixture of 2-t-butyl-4-methoxyphenol and 3-t-butyl-4-methoxyphenol), botanical oils, mineral oils, surfactants, aliphatic acids or their esters, etc.

The base for toxic baits may comprise food (e.g. grain powders, starch, essential oils, sugar, crystalline cellulose), an antioxidant (e.g. dibutylhydroxytoluene, butylhydroxyanisole, nordihydroguaiaretic acid), a preservative (e.g. dehydroacetic acid), a mis-feed inhibitor (e.g. red pepper powders), a flavoring agent (e.g. cheese flavor, onion flavor), etc.

The thus formulated preparation may be applied as such or in a form of dilution with water. Further, such preparation may comprise additionally or be used simultaneously with other insecticides, nematocides, acaricides, soil disinfectants, fungicides, herbicides, plant growth regulators, synergistic agents, fertilizers, soil improvers, etc.

The dosage of the hydrazone compound (I) as the insecticide for agriculture is generally from about 5 to 500 grams per 10 are. When applied as an emulsifiable concentrate, a wettable powder or a flowable, the concentration of the active ingredient may be normally from about 1 to 500 ppm after dilution with water. In case of such a preparation as dusts, granules, etc., the application may be made as such without dilution. As the insecticide for household or sanitary use, such a preparation comprising the hydrazone compound (I) as an emulsifiable concentrate, a wettable powder or a flowable is applied after dilution with water in a concentration of the active ingredient being generally from about 1 to 500 ppm. In case of such a preparation as an oil spray, an aerosol, a fumigant or toxic baits, it may be applied as such, i.e. without dilution.

The amount and concentration of the active ingredient are not limited to the above specified ranges and may be changed depending on the preparation form, the application time, the locus to be applied, the application mode, the species of insects, the degree of damage, etc.

Some practical embodiments of the invention are illustratively shown in the following Production Examples, Formulation Examples and Test Examples wherein % and part(s) are by weight.

PRODUCTION EXAMPLE 1

A mixture of 4-chloro-4'-trifluoromethylsulfonyloxybenzophenone hydrazone (300 g; 0.79 mmol) and N,N-dimethylacetamide dimethylacetal (127 g; 0.95 mmol) was heated under reflux at 120° C. for 5 hours, followed by concentration of the reaction mixture under reduced pressure to give the hydrazone compound (I) (350 g) as a yellow oil. $n_D^{22.5}$ 1.5964. The oil was allowed to stand at room temperature for 2 weeks for solidification. m.p., 79–81° C.

PRODUCTION EXAMPLE 2

A mixture of 4-chloro-4'-trifluoromethylsulfonyloxybenzophenone (300 mg; 0.83 mmol), N,N-dimethylacetamide hydrazone (233 mg; 2.06 mmol), acetic acid (0.3 ml) and ethanol (10 ml) was heated under reflux for 56 hours, followed by concentration of the reaction mixture under reduced pressure. The reaction mixture was diluted with methylene chloride (100 ml), washed with 2.5 N aqueous sodium hydroxide and water, dried over anhydrous sodium sulfate and concentrated under reduced pressure to give the hydrazone compound (I) (320 mg) as a yellow oil, which was allowed to stand at room temperature for 2 weeks for solidification. The physical constant of this product was identical to that of the product obtained in Production Example 1.

PRODUCTION EXAMPLE 3

A mixture of 4-chloro-4'-trifluoromethylsulfonyloxybenzophenone-N'-acetylhydrazone (300 mg; 0.71 mmol), phosphorus pentachloride (163 mg; 0.78 mmol) and p-xylene (5 ml) was heated under reflux for 10 hours under nitrogen stream. After completion of the reaction, the reaction mixture was cooled to 5 to 10° C., and under vigorous stirring, 50% aqueous dimethylamine (5 ml) was added thereto all at once, followed by stirring at room temperature for 2 hours. The xylene layer was separated from the resultant mixture, washed with water, dried over anhydrous sodium sulfate and concentrated under reduced pressure. The oily concentrate thus obtained was crystallized from methanol to give the hydrazone compound (I) (312 mg) as yellow crystals. The physical constant of this product was identical to that of the product obtained in Production Example 1.

PRODUCTION EXAMPLE 4

A mixture of 4-chloro-4'-trifluoromethylsulfonyloxybenzophenone-N'-acetylhydrazone (300 mg; 0.71 mmol), phosphorus oxychloride (120 mg; 0.78 mmol) and toluene (5 ml) was heated under reflux for 10 hours under nitrogen stream. After completion of the reaction, the reaction mixture was cooled to 5 to 10° C., and under vigorous stirring, 50% aqueous dimethylamine (5 ml) was added thereto all at once, followed by stirring at room temperature for 15 hours. The toluene layer was separated from the reaction mixture, washed with water, dried over anhydrous sodium sulfate and concentrated under reduced pressure. The oily concentrate thus obtained was crystallized from methanol to give the hydrazone compound (I) (160 mg) as yellow crystals. The physical constant of this product was identical to that of the product obtained in Production Example 1.

PRODUCTION EXAMPLE 5

A mixture of 4-chloro-4'-trifluoromethylsulfonyloxybenzophenone-N'-(1-chloroethylidene)hydrazone (300 mg; 0.68 mmol) and benzene (5 ml) was vigorously stirred, and 50% aqueous dimethylamine (5 ml) was added thereto all at once at a temperature of 5 to 10° C., followed by stirring at room temperature for 2 hours. The same post-treatment as in Production Example 3 gave the hydrazone compound (I) (297 mg) as yellow crystals. m.p., 79–81° C.

PRODUCTION EXAMPLE 6

A mixture of 4-chloro-4'-trifluoromethylsulfonyloxybenzophenone-N'-[1-(dichlorophosphonyloxy)ethylidene]hydrazone (300 mg; 0.56 mmol) and toluene (5 ml) was vigorously stirred, and 50% aqueous dimethylamine (5 ml) was added thereto all at once at 5 to 10° C., followed by stirring at room temperature for 15 hours. The same post-treatment as in Production Example 4 gave the hydrazone compound (I) (120 mg) as yellow crystals. The physical constant of this product was identical to that of the product obtained in Production Example 1.

FORMULATION EXAMPLE 1

The hydrazone compound (I) (0.2 part), xylene (2 parts), dimethylformamide (2 parts) and lamp oil (95.8 parts) are well mixed to make an oil spray.

FORMULATION EXAMPLE 2

The hydrazone compound (I) (10 parts), polyoxyethylene styrylphenyl ether (14 parts), calcium dodecylbenzenesulfonate (6 parts), xylene (35 parts) and dimethylformamide (35 parts) are well mixed to make an emulsifiable concentrate.

FORMULATION EXAMPLE 3

The hydrazone compound (I) (20 parts), fenitrothion (0,0-dimethyl-0-(3-methyl-4-nitrophenyl)phosphorothioate) (10 parts), calcium ligninsulfonate (3 parts), sodium laurylsulfate (2 parts) and synthetic hydrated silica (65 parts) are well mixed in a pulverizer to make a wettable powder.

FORMULATION EXAMPLE 4

The hydrazone compound (I) (1 part), carbaryl (1-naphthyl N-methylcarbamate) (2 parts), kaolin clay (87 parts) and talc (10 parts) are well mixed in a pulverizer to make a dust.

FORMULATION EXAMPLE 5

The hydrazone compound (I) (5 parts), synthetic hydrated silica (1 part), calcium ligninsulfonate (2 parts), bentonite (30 parts) and kaolin clay (62 parts) are well mixed in a pulverizer. To the resultant mixture, water is added, and the resulting mixture is kneaded well and granulated by the aid of a granulator, followed by drying to give granules.

FORMULATION EXAMPLE 6

The hydrazone compound (I) (0.05 part), tetramethrin (N-(3,4,5,6-tetrahydrophthalimido)methyl chrysanthemate) (0.2 part), resmethrin (5-benzyl-3-furylmethyl (±)-cis,trans-chrysanthemate) (0.05 part), xylene (7 parts) and deodorized lamp oil (42.7 parts) are well mixed and charged into an aerosol container. Upon attachment of a valve, a pressurizing agent (LPG) (50 parts) is charged through the valve to make an aerosol.

FORMULATION EXAMPLE 7

The hydrazone compound (I) (20 parts), formalin condensate of sodium naphthalenesulfonate (3 parts) and water (75 parts) are well mixed, and methyl cellulose (2 parts) as a thickening agent is added thereto to make flowables.

FORMULATION EXAMPLE 8

The hydrazone compound (I) (1 part) is admixed with sesame oil (3 parts), and butyl hydroxyanisole (0.03 part), dehydroacetic acid (0.1 part), black sugar (10 parts), crystalline cellulose (30 parts) and potato starch (55.87 parts) are added thereto. The resultant mixture is stirred uniformly, pressed with a load of 15 kg/cm$^2$ and tableted into a bait (diameter, ca. 30 mm) of about 4 g.

The following Test Examples show some typical test data indicating the excellent insecticidal activity of the hydrazone compound (I). The compounds used for comparison are shown in Table 1 below:

TABLE 1

| Compound symbol | Structure | Remarks |
|---|---|---|
| (A) | Cl—C$_6$H$_4$—C(=N—N=CH—N(CH$_3$)$_2$)—C$_6$H$_4$—OSO$_2$CF$_3$ | EP-A1-026040 |

TABLE 1-continued

| Compound symbol | Structure | Remarks |
|---|---|---|
| (B) | Cl—C₆H₄—C(=N—NHC(=O)—OC₂H₅)—C₆H₄—OSO₂CF₃ | EP-A1-003913 |
| (C) | (C₂H₅O)₂P(=S)—O—N=C(—C₆H₅) (isoxazoline structure) | Isoxathione (commercial insecticide) |

TEST EXAMPLE 1

An emulsifiable concentrate prepared according to Formulation Example 2 was diluted with water to make a 20,000 fold dilution (5 ppm). The dilution (20 ml) was sprayed to the rice plant grown in a plastic cup (diameter, 7 cm; length, 7 cm) in which twenty 3–4 instar larvae of rice leafroller (*Cnaphalocrocis medinalis*) was inoculated on the previous day. After three days, mortality (%) of the larvae was observed with two replications. The results are shown in Table 2.

TABLE 2

| Test compound | Mortality (%) |
|---|---|
| Hydrazone compound (I) | 98 |
| (A) | 13 |
| (B) | 62 |
| (C) | 23 |
| Untreated | 0 |

TEST EXAMPLE 2

An emulsifiable concentrate prepared according to Formulation Example 2 was diluted with water to make a 1,000 fold dilution (100 ppm), and the dilution was sprayed over a cabbage field (each plot, 3.9 m²) with a spray volume of 1.5 liters. Propagation of the larvae of diamondback (*Plutella xylostella*) in cabbage hills (each 10 hills per field) before the treatment as well as 8, 14, 21, 28 and 35 days after the treatment was observed with three repetitions, and the control value was calculated according to the following equation:

$$\text{Control value} = \left(1 - \frac{Cb \sum_{i=1}^{n} Tai}{Tb \sum_{i=1}^{n} Cai}\right) \times 100$$

n: number of observation after treatment
Cb: number of larvae before treatment in untreated plot
Cai: number of larvae on the (i)th observation after treatment in the untreated plot
Tb: number of larvae before treatment in treated plot
Tai: number of larvae on the (i)th observation after treatment in the treated plot The results are shown in Table 3.

TABLE 3

| Test compound | Control value |
|---|---|
| Hydrazone compound (I) | 85.5 |
| (A) | 2.4 |

TEST EXAMPLE 3

An acetone solution of the hydrazone compound (I) was dropwise added to a solid fertilizer (0.5 g) for breeding mouse or rat (Solid Fertilizer "CE-2" manufactured by Nihon Kurea K. K.) to make a 1% treated bait. The thus obtained bait was put in a small cap (diameter, 3 cm) and charged in a polyethylene container (diameter, 11 cm; height, 10.5 cm) together with another cup containing the non-treated bait, water and a paper shelter, where 20 adults of German cockroach (each ten adults of male and female cockroach) were released and the wriggling mortality (%) was observed 3 days thereafter. The results are shown in Table 4.

TABLE 4

| Test compound | Wriggling mortality (%) |
|---|---|
| Hydrazone compound (I) | 100 |
| (A) | 65 |
| (B) | 30 |
| Untreated | 0 |

TEST EXAMPLE 4

An emulsifiable concentrate prepared according to Formulation Example 2 was diluted with water to make a 50 ppm dilution, and the dilution (1 ml) was dropped onto a filter tightly placed at the bottom of a polyethylene cup (diameter, 5.5 cm), where 20 to 30 eggs of southern cornroot worm and a sprouting grain of corn were charged. The container was sealed with a cap, and 8 days thereafter mortality (%) was observed on the following criteria:
a: 100%
b: 90–less than 100%
c: less than 90%

The results are shown in Table 5.

TABLE 5

| Test compound | Mortality (%) |
|---|---|
| Hydrazone compound (I) | a |
| (A) | c |

What is claimed is:

1. A compound of the formula:

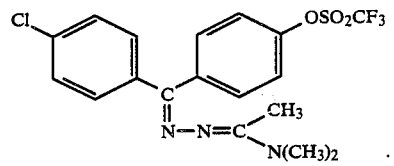

2. An insecticidal composition which comprises as an active ingredient an insecticidally effective amount of the compound according to claim 1, and an insert carrier or diluent.

3. A method for controlling or exterminating insects which comprises applying as the active ingredient an insecticidally effective amount of the compound according to claim 1 to the locus where insects propagate.

* * * * *